US012594356B2

(12) United States Patent
Slotkin et al.

(10) Patent No.: US 12,594,356 B2
(45) Date of Patent: Apr. 7, 2026

(54) PROACTIVE AIR/SURFACE DECONTAMINATION SYSTEM AND DEVICES

(71) Applicant: Radical Clean Solutions Ltd., Long Beach, NY (US)

(72) Inventors: Roger Slotkin, Long Beach, NY (US); Ralph T. Kubitzki, Plantation, FL (US)

(73) Assignee: Radical Clean Solutions Ltd., Long Beach, NY (US)

( * ) Notice: Subject to any disclaimer, the term of this patent is extended or adjusted under 35 U.S.C. 154(b) by 710 days.

(21) Appl. No.: 17/861,181

(22) Filed: Jul. 9, 2022

(65) Prior Publication Data

US 2023/0173130 A1    Jun. 8, 2023

Related U.S. Application Data

(63) Continuation-in-part of application No. 17/545,919, filed on Dec. 8, 2021.

(51) Int. Cl.
*A61L 9/20*      (2006.01)
*A61L 2/10*      (2006.01)

(52) U.S. Cl.
CPC ................... *A61L 9/20* (2013.01); *A61L 2/10* (2013.01); *A61L 2209/111* (2013.01); *A61L 2209/211* (2013.01)

(58) Field of Classification Search
CPC ........ A61L 2/10; A61L 9/20; A61L 2209/111; A61L 2209/12; A61L 2209/15; A61L 2209/20
See application file for complete search history.

(56) References Cited

U.S. PATENT DOCUMENTS 2,945,554 A     7/1960   Berly
5,968,455 A  * 10/1999   Brickley ................... A61L 9/20
                                                      362/267
(Continued)

FOREIGN PATENT DOCUMENTS

JP        2010080195 A     4/2010
WO  PCT/US2022/051886 A     5/2023

OTHER PUBLICATIONS

LSE (Light Spectrum Enterprises); "Shop UV Lighting-GPH457T5L/ 4P Ultraviolet UV Lamp Bulb 4-pin Base 18" GPH457T5"; 1300 Industrial Blvd.—Ste B3, Southampton, PA 18966.
(Continued)

*Primary Examiner* — Timothy C Cleveland
(74) *Attorney, Agent, or Firm* — Alfred M. Walker; Thomas A. O'Rourke; James Bongiorno

(57)            ABSTRACT

A system for decontaminating/neutralizing breathable air and surfaces in an occupied enclosed space, i.e., aircraft, rail and road vehicles, in buildings and other human occupied spaces, includes mounting an atmospheric hydroxyl radical generator along an inside surface of an occupied space having respective air inlets and air outlets. The hydroxyl radical generator includes a polygonal housing supporting a plurality of spaced crystal-spliced UV optics medical grade pure quartz, which emit/irradiate ultraviolet in the nanometer wavelength/ultraviolet spectrum of between 100 and 400 nanometers for deactivating and neutralizing atmospheric chemicals and pathogens in breathable air and surfaces. The hydroxyl radicals contact the walls of the reaction chamber housing. The hydroxyl radicals become created and excited to react quickly with impurities including VOC, virus, bacteria and fungi, rendering them inactivated and neutral. The breathable air passes through the polygonal housing and
(Continued)

is decontaminated and neutralized of impurities before entering the occupied enclosed space.

11 Claims, 6 Drawing Sheets

(56) References Cited

U.S. PATENT DOCUMENTS

| | | | |
|---|---|---|---|
| 6,497,840 | B1 | 12/2002 | Palestro et al. |
| 6,613,277 | B1 | 9/2003 | Monagan |
| 6,805,733 | B2 | 10/2004 | Engel et al. |
| 7,837,933 | B2 | 11/2010 | Sevack et al. |
| 7,976,195 | B2 | 7/2011 | Engel et al. |
| 7,988,923 | B2 | 8/2011 | Fink et al. |
| 8,226,899 | B2 * | 7/2012 | Woodbridge ............. A61L 9/20 |
| | | | 422/186.04 |
| 8,252,099 | B2 | 8/2012 | Worrilow |
| 8,252,100 | B2 | 8/2012 | Worrilow |
| 8,545,753 | B2 | 10/2013 | Sevack et al. |
| 8,747,753 | B2 | 6/2014 | Engel et al. |
| 9,168,323 | B2 | 10/2015 | Morneault |
| 9,522,210 | B2 | 12/2016 | Worrilow |
| 9,675,725 | B2 | 6/2017 | Worrilow |
| 9,884,135 | B2 | 2/2018 | Bystrzynski et al. |
| 9,956,306 | B2 | 5/2018 | Brais et al. |
| 9,980,748 | B2 | 5/2018 | Worrilow |
| 10,857,249 | B2 | 12/2020 | Brais et al. |
| 11,103,611 | B2 | 8/2021 | Elde et al. |
| 2008/0073565 | A1 | 3/2008 | Jeon |
| 2008/0279733 | A1 * | 11/2008 | Glazman ................. F24F 8/192 |
| | | | 422/243 |
| 2015/0114822 | A1 | 4/2015 | Greco |
| 2017/0225973 | A1 | 8/2017 | Henderson et al. |
| 2020/0084983 | A1 | 3/2020 | Liang et al. |
| 2020/0129972 | A1 | 4/2020 | Ozaki et al. |
| 2021/0339184 | A1 * | 11/2021 | Hourani .................... F24F 8/10 |
| 2022/0074615 | A1 * | 3/2022 | Richardson .............. F24F 8/22 |

OTHER PUBLICATIONS

Hao Chen, et al.; "A Hydroxyl radical detection system using gas expansion and fast gating laser-induced fluorescence techniques"; The Research Center for Eco-Environmental Sciences, Chinese Academy of Sciences; Journal of Environmental Sciences 65 (2018) 190-200; published by Elsevier B.V.; http//dx.doi.org/10.1016/i.jes.2017.03.012.

* cited by examiner

PROACTIVE AIR/SURFACE DECONTAMINATION SYSTEM AND DEVICES

RELATED APPLICATIONS

This application is a continuation-in-part of application Ser. No. 17/545,919, filed Dec. 8, 2021 (the '919 application), and claims priority in part therefrom, pursuant to 35 U.S.C. 120.

FIELD OF THE INVENTION

The present invention relates use of a harmonic biomimicry nonchemical photonic process that results in the export of desired atmospheric hydroxyls at precisely the same rate as nature provides (2.6 million per cubic Centimeter—NASA), to neutralize toxic chemicals and pathogens in breathable air/surfaces in stationary or moving human occupied spaces.

BACKGROUND OF THE INVENTION

Ultraviolet light (UV) delivery in the form of directing ultraviolet light on unsanitary surfaces as germicides, bactericides and viricides are disadvantageous because, upon exposure to seating fabrics in aircraft and related airborne vehicles, such as helicopters, seating fabrics in mass transit rail and road vehicles, in building interior ducts and wall surfaces and other human occupied spaces, the ultraviolet light compromises fabrics and doesn't penetrate into crevices between, or in, passenger seats or flight deck seats, located in the flight deck, separately sealed away from the air of the passenger cabin, or in seating fabrics in mass transit rail and road vehicles, in building interior ducts and wall surfaces and other human occupied spaces. Delivery of ultraviolet light for sanitation is limited because the ultraviolet light is only as effective as the actual line of sight of the ultraviolet waves.

DESCRIPTION OF THE PRIOR ART

Methods of Producing Atmospheric Hydroxyls

In the field of physics there are, to date, only a few processes in a device that generates an atmospheric hydroxyl that purportedly are useful in removing contaminants from breathable air. In theory the NASA device produces the hydroxyl in a photo catalytic oxidation (PCO) process, by emitting an ultraviolet irradiation of 254 nanometers as it interfaces with titanium dioxide ($TiO_2$) plating. In theory, the hydroxyl is produced only at the interface site of contact at the surface of the $TiO_2$. The hydroxyl does not exit the airstream and does not have any downstream interaction. Minimal air flow must be maintained at approximately 120 cfm. Typical HVAC systems utilize faster air movement at approximately 2000 cfm and this would not allow for the theoretical hydroxyl to form.

OBJECTS AND SUMMARY OF THE INVENTION

In contrast, the present invention uses airborne hydroxyl radical molecules, which are of very small molar size and can occupy almost any given space. They can occupy dark crevices that ultraviolet line of sight cannot get access to. The present invention allows for a "Harmonic" of photonic UV frequencies to be applied within a hydroxyl producing reaction chamber. The feed stock is ambient water vapor in air which will have relative humidity, this humidity is the feed stock for the reaction chamber to produce the atmospheric hydroxyl.

This action is called "Bio-Mimicry". The present invention process is a totally green, environmentally friendly nonchemical process that results in the export of the desired atmospheric hydroxyl at precisely the same rate as nature provides, namely, at 2.6 million per cubic centimeter. The atmospheric hydroxyl process begins by exposing ambient water vapor to special UV optics having hydroxyl activation portions made of medical grade pure quartz material. The optics are designed to emit/irradiate Ultraviolet irradiation in the nanometer wavelength/Ultraviolet spectrum of between 100 and 400 nanometers, thereby producing the hydroxyls at the aforementioned quantity of 2.6 million hydroxyls per cubic centimeter, as provided in nature. This is a novel improvement over prior art NASA PCO based technology.

Hydroxyl are groups having the radical "—OH" and are represented by the symbol —OH or HO—, which can have a negative charge or be neutral. The hydroxyl functional group includes one hydrogen atom which is covalently bonded to one oxygen atom. Hydroxyl radicals are very reactive, which react quickly to hydrocarbons, carbon monoxide molecules and other air impurities, such as volatile organic compounds, (VOC), virus, bacteria and fungi.

Many closed HVAC air systems can harbor microscopic bacteria, virus (i.e., Covid-19) and fungi.

For example, aircraft and other airborne transportation vehicles, such as helicopters, seat fabrics on mass transit rail and road vehicles, in building ducts and wall surfaces and other human occupied spaces, can harbor bacteria and virus in the separate, circulated air systems.

Therefore, the present invention is a unique and novel application method for the delivery of safe and natural hydroxyl radicals into breathable air volume containers such as airline flight deck or passenger cabins, and the contents therein, seat fabrics on mass transit rail and road vehicles, in building ducts and wall surfaces and other human occupied spaces. To be considered as well are upholstered chair seats, benches, contact surfaces such as grab bars, handles, etc.

In the present invention, the atmospheric hydroxyl radicals are generated in closed multi-sided housing, preferably polygonal, having therein two or more parallel UV optics which are multi segmented with crystal, so that when enabled, the hydroxyl radicals are generated. Hydroxyls are reactive and short lived, however the closed housing reaction chamber preferably has polygonal interior walls, so that the hydroxyl radicals will bounce against the walls so as to decontaminate within the reaction chamber as well as downstream in open air areas. Breathable air is then directed through the closed housing, so that the created and excited radicals will react quickly to air and surface impurities, such as pathogens and VOC's, rendering them neutral.

The UV optics are tubular, medical grade pure quartz. The optics are designed to emit/irradiate Ultraviolet irradiation in the nanometer wavelength/Ultraviolet spectrum of between 100 and 400 nanometers.

A multi wave 'Harmonic' is created via a multiwavelength nanometer configured optic irradiation. This configuration results in the creation of the desired atmospheric hydroxyl within the hydroxyl generator reaction chamber, which is a multi-sided reaction chamber, designed in such a way as to optimize atmospheric downstream hydroxyl production, such as for example in a polygonal-shaped housing. This multi-sided reaction chamber enables the desired atmospheric hydroxyl to be injected downstream to affect positive change. The positive change is the control/neutralization of pathogens and VOC's.

The —OH formed hydroxyl molecule is the capacitor that donates electrons to the targeted pathogen, whereupon the pathogen is therefore neutralized by the 'Electron Voltage (eV')' capacitance carried by the hydroxyl. The eV is donated at the point of contact with the pathogen.

VOC's are neutralized through the action of Bond Dissociation Energy (BDE). The capacitance of the charged hydroxyl is sufficient so as to take out of phase (decomposition) of any airborne molecular or compound structure. In Phase VOC chemistry can be harmful, therefore out-of-phase atomic airborne structures are now neutral and cannot recombine. The exception to this rule would be the recombination of water vapor, carbon dioxide and lastly oxygen (O2).

This reaction sequence is essential to all life, in that water vapor feeds all life, and carbon dioxide (CO2) is necessary/essential for plant life and oxygen (O2) is essential for air breathers such as human, other animals and forms of living organisms.

EXAMPLES

Because exposure of the UV light is problematic for human eyes, the interior chamber holding the reaction chamber is custom designed to arrest UV light escaping and to maximize atmospheric hydroxyl discharge. Refraction color can come out of the unit with the generated, activated hydroxyls, but never direct UV light.

Available hydrogen is low in our natural environment, so one must add electron rings to obtain optimal amplitude as opposed to adding hydrogen for increased hydroxyl production.

The polygonal shape of the reaction chamber enhances the total ability of the chamber to produce the desired atmospheric hydroxyl.

It is essential that the atmospheric hydroxyls be produced by the exposure of ambient water vapor within a confined refractive generator chamber housing to prevent diminution of the atmospheric hydroxyls. In contrast, the prior art of SanUVox, by using outward facing reflectors but no confined generator chamber housing, causes a drastic diminution of the desired hydroxyl production.

In contrast the present invention, by using the polygon shaped reaction chamber, has categorically enhanced atmospheric hydroxyl production.

For safety, an air pressure safety switch is provided, so that when air flow is not detected, this unit will be dormant. A Micro Switch shuts down all systems should the device be opened when unit is in the ON/RUN position.

The hydroxyl generator includes a housing having an air inlet at one end and air outlet at an opposite end thereof, wherein the housing contains a plurality of spaced crystal-spliced UV optics, the UV optics being tubular, medical grade pure quartz optics designed to emit/irradiate ultraviolet in the nanometer wavelength/ultraviolet spectrum of between 100 and 400 nanometers for deactivating chemicals and pathogens in the breathable air for the respective flight deck and passenger compartments, on mass transit rail and road vehicles, in building ducts and other human occupied spaces. The air inlet at one end and the air outlet at an opposite end of the housing are provided for exposing ambient water vapor to the plurality of spaced crystal-spliced UV optics, to generate the hydroxyls. Preferably, the housing comprises a lengthwise extending hollow housing having a polygon shape in cross section, with adjoining lengthwise extending flat walls.

BRIEF DESCRIPTION OF THE DRAWINGS

The present invention can best be understood in connection with the following drawings, which are not deemed to be limiting in scope.

DETAILED DESCRIPTION OF THE DRAWINGS

Figures 1, 2:
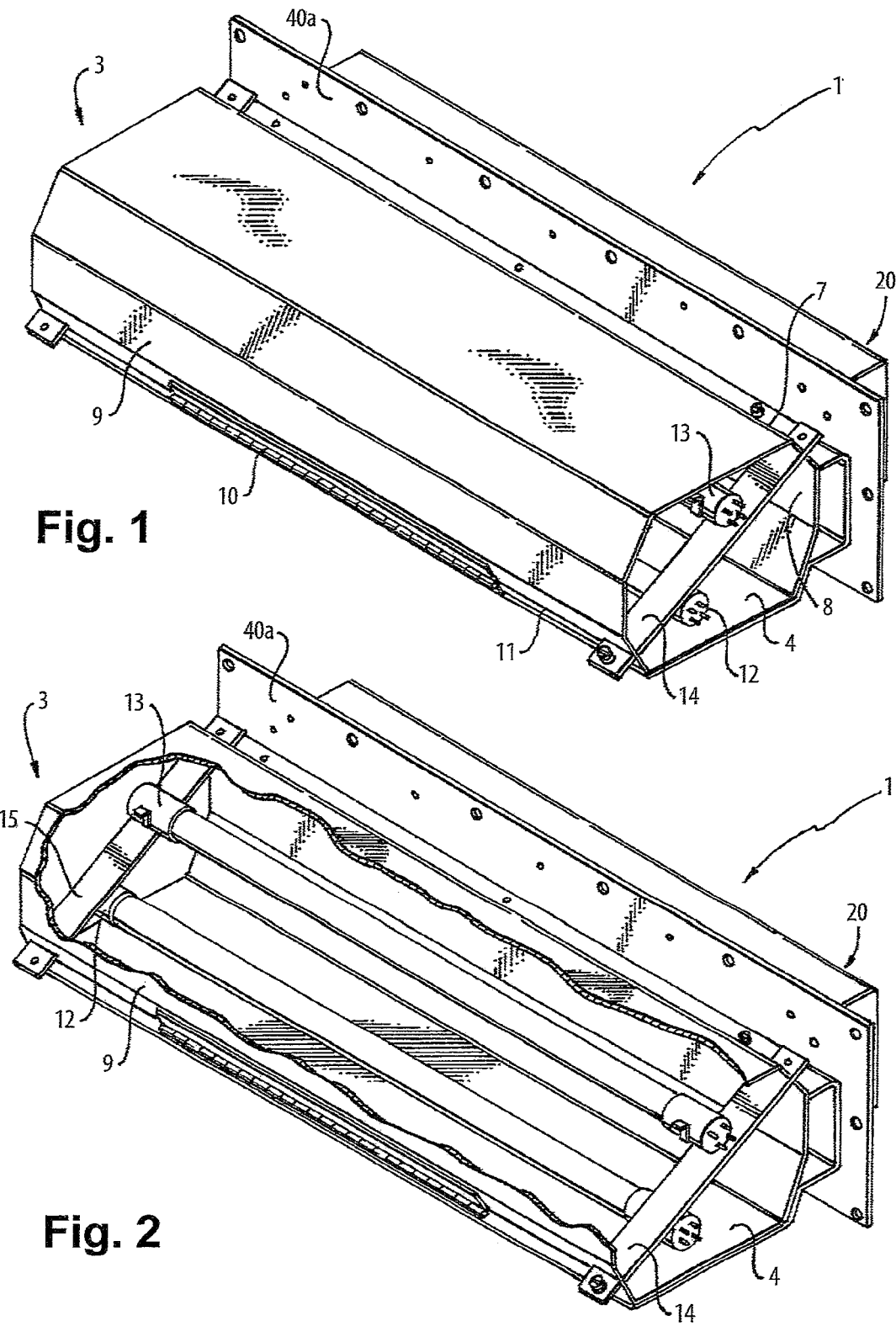
FIG. 1 is a perspective view of a polygonal hydroxyl generator shown in a closed position.
FIG. 2 is a perspective view of the hydroxyl generator of FIG. 1 shown in partial crossection with an open view of the interior of the hydroxyl generator.

FIG. 1 shows a hydroxyl generator 1, including a polygonal-shaped housing, including a bracket brace 14 for supporting crystal-spliced UV optics 12 and 13 within respective C-shaped spring clasps 12a and 13a, which are each respectively mounted on bracket brace 14, which are mounted parallel lengthwise to each other inside the clamshell hexagon housing, but staggered so that UV optic 12 is on a different side of the bracket 14 from the side on which UV optic 13 is located, wherein the crystal spliced UV optics 12 and 13 each have a length that runs substantially the entire length of the housing of the hydroxyl generator 1. A preferred example for the crystal-spliced UV optics 12 and 13 is the GPH457T5L/4P UV Optic 4-pin Base 18" GPH457T5 of Light Spectrum Enterprises of Southampton these optics 12 and 13 are typically 18 inches long and are made of quartz. The tubular optics 12 and 13 are composed of pure Medical Grade quartz crystal in the portion of the optics which creates the hydroxyls. The present invention adds additional frequencies to the pure crystal optics. These tubular optics 12 and 13 generate 'Harmonic' bio-mimicry nonchemical process of the present invention which enables the production of desired atmospheric hydroxyls at a rate commensurate with the VOC/Bio loading in that particular space to be treated with the hydroxyls.

In contrast to the medical grade quartz tubular optics, it is noted that total glass tubes cannot be used when generating UV. The glass would simply be vaporized. Some companies use a fusion of glass and quartz crystal, which is not optimal as the glass portion creates a frequency that actually attracts contaminants. This problematic action neutralizes the desired UV action. Such a fusion lamp of glass and quartz crystal is cheaper to produce, however the poor performance of the lamp would be the end result.

Figure 3:
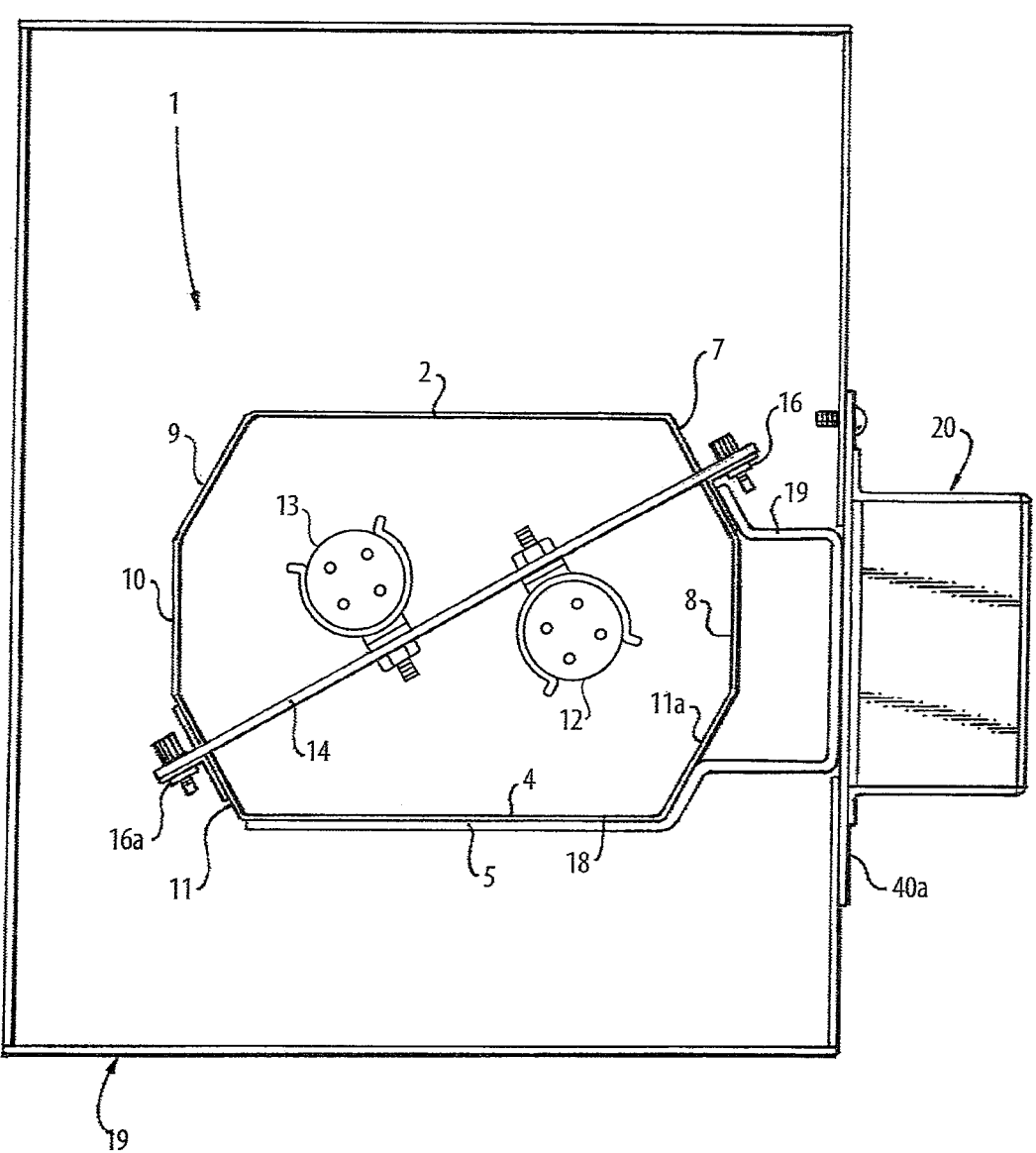
FIG. 3 is an end view in crossection of the hydroxyl generator of FIG. 1, with two UV optics for generating hydroxyl radicals.
Figure 4:
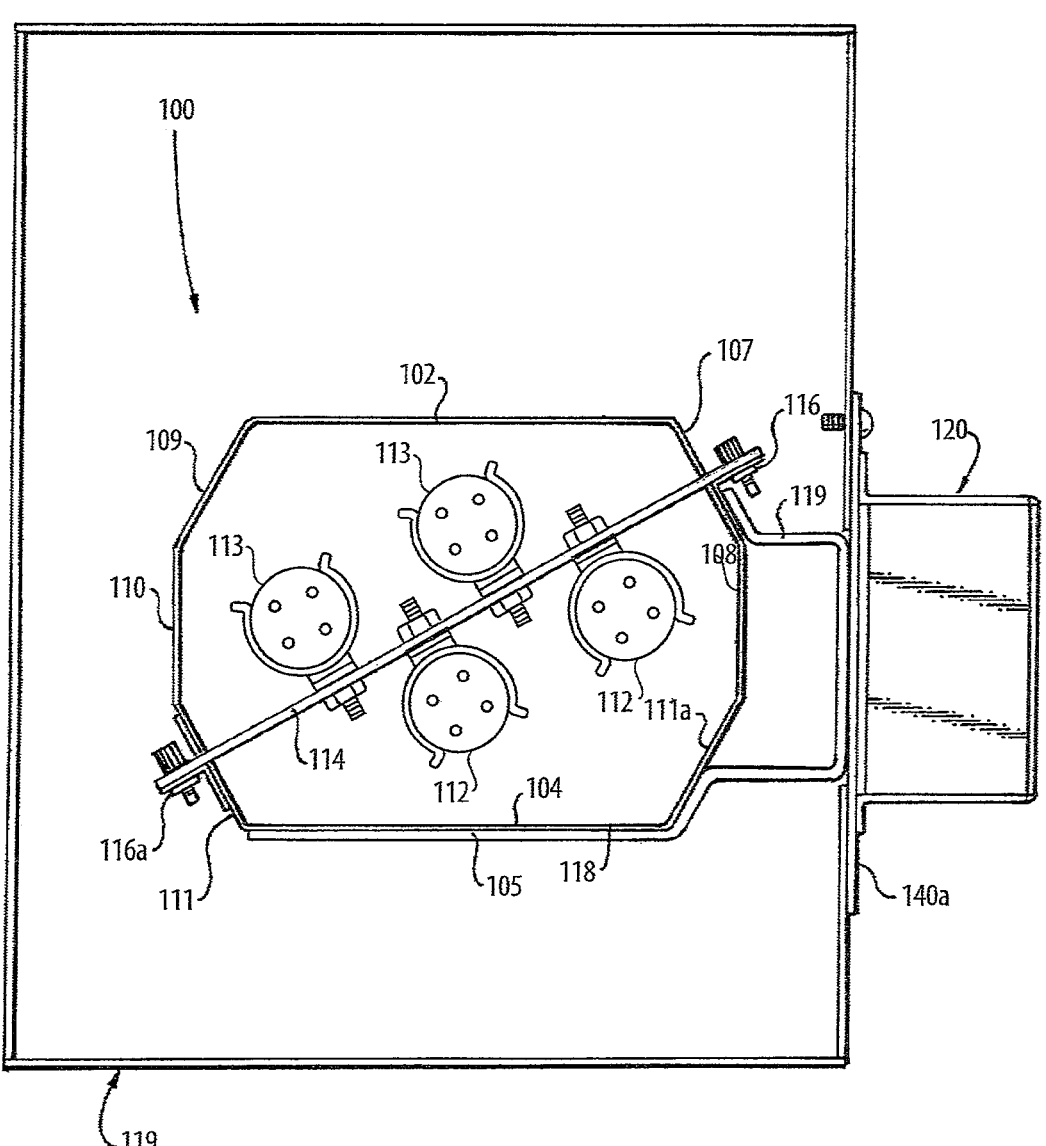
FIG. 4 is a crossectional end view of an alternate embodiment for a hydroxyl generator, showing four UV hydroxyl generator optics within the polygonal hydroxyl generator.

Other similar Medical Grade quartz tubed UV optics can be used. The optics 12 and 13 are preferably symmetrically positioned in the housing of the hydroxyl generator 1, as shown in FIGS. 3 and 4 to operate most efficiently, but where in FIG. 3 the crystal spliced UV optics 12 and 13 are staggered so that UV optic 12 is on a different side of the bracket brace 14 from the side on which UV optic 13 is located. FIG. 4 shows an alternate embodiment where there are two pairs of UV optics, namely 112,113 and 112*a*, 113*a*. The UV optics 112, 113 are staggered to the right on one bottom side of the horizontal bracket brace 114, but are separated by upright bracket brace 114. Likewise, UV optics 112*a* and 113*a* are respectively staggered to the left on the opposite top side of the horizontal bracket brace 114, also separated from each other by upright bracket brace 114. Optics pairs 112, 113 and 112*a*, 113*a* are supported within pairs of respective C-shaped spring clasps 112*c*,113*c* and 112*d*, 113*d*, which pairs of optics 112, 113 and 112*a*, 113*a* are each respectively mounted on bracket brace 114, and which pairs of optics 112, 113 and 112*a*, 113*a* are mounted parallel lengthwise to each other inside the clamshell hexagon housing 1.

The clamshell hexagon housing hydroxyl generator 1 has a clamshell configuration, including a clamshell top wall 2, upper side walls 7, 8, 9 and 10, a hinge 6 for opening the polygonal clamshell housing 1 and a bottom clamshell portion, including a bottom wall 4 and angle-oriented walls 11 and 11*a*, whereby the polygon housing opens hinge 6 to expose the inside of the hydroxyl generator 1 for maintenance and/or repair. In addition, the polygon hydroxyl generator enclosure can be removed from the air duct wall 40A for such maintenance and repair. The hydroxyl generator also includes an adjacent electronic control box 20, which is attachable to the clamshell housing of the hydroxyl generator 1. Alternatively, as shown in FIGS. 3 and 4, the electronic control box 20 is preferably located outside of the air path, which may be a duct or other conduit. It can alternatively be attached outside of the duct. It communicates with the UV optics wirelessly. The reason for the polygon shape is that the hydroxyl generators generated by the crystal-spliced UV optics 12 and 13 are scattered upon being generated by the optics 12 and 13, but they dissipate quickly if not activated by contact with reflective non-absorbent surfaces inside the respective walls of the polygon. The purpose of the polygon shape is that when the hydroxyl radicals are generated, they are emitted radially in all directions from the UV crystal-spliced optics 12 and 13 and normally would dissipate when scattered radially from the optics. In order to permit the hydroxyl radicals to maintain their desired electron charge and ability to contact and inactivate mold, volatile organic compounds, pathogens, bacteria, virus, etc., they need to reflect and refract off of the reflective non-absorbent walls continuously, within the reaction chamber confined space. As atmospheric hydroxyls are being activated by being created and excited in back-and-forth activity, the air inside the air duct/plenum 40*a* will contact the activated hydroxyl radicals with the end result of the neutralization of any impurities, such as VOCs, virus, bacteria, fungi, etc., in the air and surfaces.

Furthermore, once these radicals are emitted, they can penetrate any crevices in any area, such as between seats of aircraft, mass transit rail and road vehicles, in building ducts and wall surfaces and other human occupied spaces, between the surfaces of seats and shelving, anywhere where ultraviolet light by itself would not be capable of eradicating the undesirable VOCs, fungi, virus, bacteria, etc. The polygon-shaped housing is strategically located within an air supply unit in an airport terminal building, or it can be located within a remote cart not located near the aircraft, on the tarmac of the airport, and preferably it may be provided in the air systems separately of an aircraft cabin, including the flight deck and the areas of the main cabin where passengers are seated. The polygon shaped housings may also be strategically located in mass transit rail and road vehicles, in building ducts and wall surfaces and other human occupied spaces As shown in the end view of FIG. 3, the inside of the polygon housing 1 is located below the field of vision within the sealed off plenum so that the ultraviolet (UV) crystal-spliced tubular optics 12 and 13 will not be exposed to the eyes of any observers. Therefore, while the hydroxyl radicals are being generated, the UV energy which create hydroxyl generation from optics 12 and 13 are completely sealed off so that when the optics 12 and 13 are operational, the UV light emanating therefrom will not penetrate outside of the polygonal housing. Baffles, optionally located outside of the hydroxyl generators, but in the vicinity of the hydroxyl generators, prevent the UV light from exposure to persons. There is no restriction regarding the active flow of the hydroxyls inside the hydroxyl generator 1 and no interference with the excitement of the hydroxyls produced by the exposure of ambient water vapor within the polygon shaped housing with the UV optics 12 and 13 irradiating light that causes the —OH radicals to form.

FIG. 4 shows an alternate embodiment for a four optic version, where polygon hydroxyl generator enclosure 101, having top wall 102, side walls 107, 108, 109, 110 of an upper shell, as well as lower walls 105, 111*a*, 111*b* of the clamshell housing. FIG. 4 also shows the electronics control box 120. The respective pairs of optics 112, 113 are supported within respective pairs of C-shaped spring clasps 112*a* and 113*a*, which are each respectively mounted on bracket brace 114, which are mounted parallel lengthwise to each other inside the clamshell hexagon housing 101. Clamshell housing 101 is openable via hinge 106.

Figure 5:
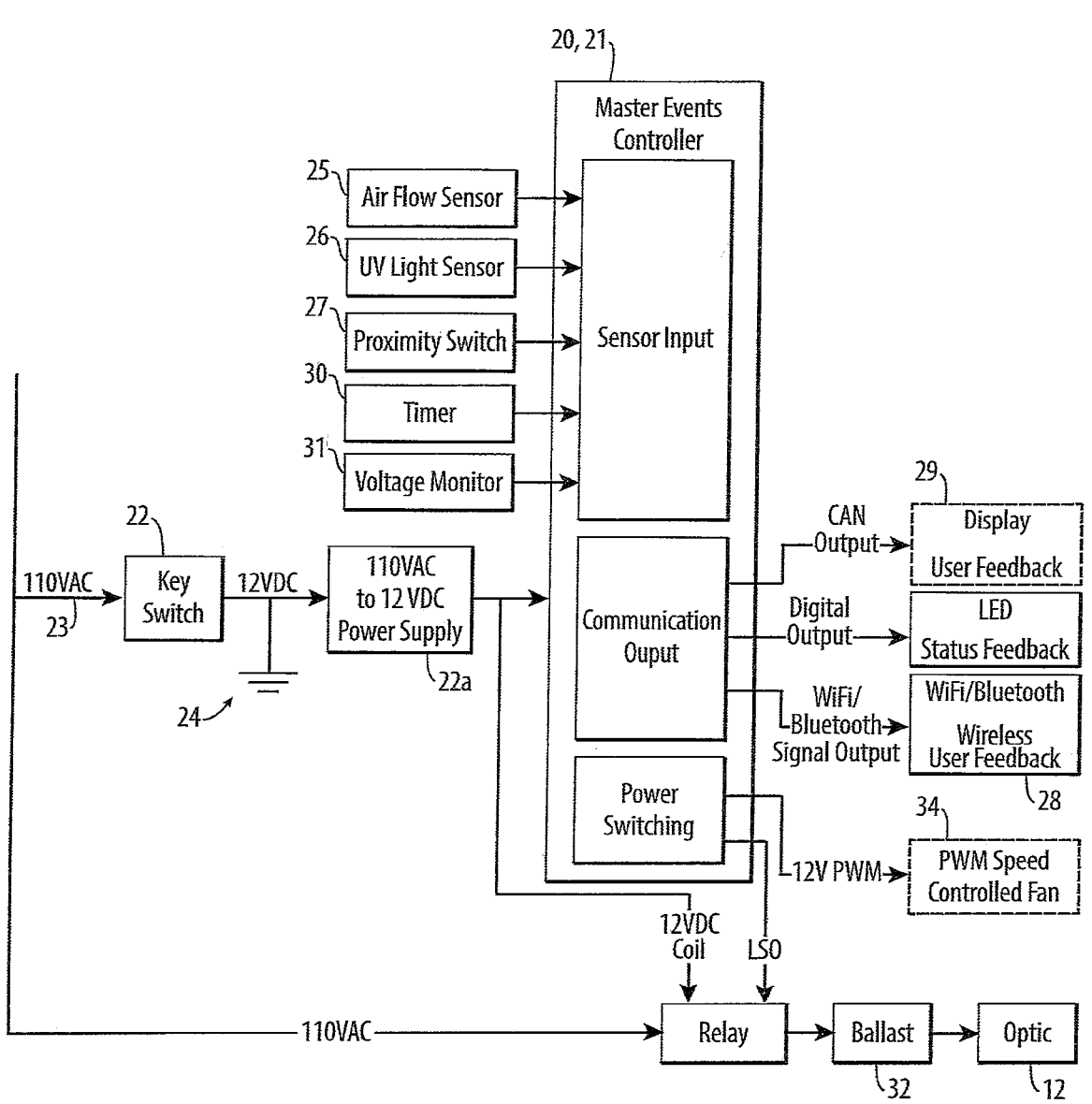
FIG. 5 is a block diagram of the electronic controls of the hydroxyl generator of FIGS. 1-3 and 4.

FIG. 5 is a block diagram showing the network and electronics of the control box 20. Initially AC power 23 of 110 VAC is converted by converter 22 to low voltage 12 VDC, or else a low voltage battery alternatively delivers 12 VDC to a secure Key Switch 22*a*, to provide power to the Master Events Controller 20, which may have a microprocessor 21. The Master Events Controller 20 also receives input from sensors, such as Air Flow Sensor 25, UV Light Sensor 26, Proximity Switch 27 (detecting opening of the enclosure), Timer 30 and Voltage Monitor Sensor 31. These sensors provide Sensor Input to the Master Events. Controller 20. Power Switching in the Master Events Controller 20 sends 12V Pulse Width Modulation data to a PWM Speed Controlled Fan 34, to send air through the hydroxyl generator unit 1 or 101, or to stop the flow of air when needed for safety and maintenance situations. The Power Switching also sends data via a Large Serve Outlet (LSO) to a Relay, which controls the Ballast 32, providing power to the Crystal UV Optics 12, which creates the needed hydroxyls within the hydroxyl generators 1 or 101. The Master Events Controller 20 also has a Communications Output, which can send data via a Controller Area Network (CAN) to a Visual Display 29 for user feedback. The Communications Output of the Master Events Controller 20 also sends digital data wirelessly as output to Status Feedback Units. The Communications Output of the Master Events Controller 20 also sends Wi-Fi/Bluetooth Signal output to Wireless input devices 28 for Wireless user feedback during use.

Figure 5A:
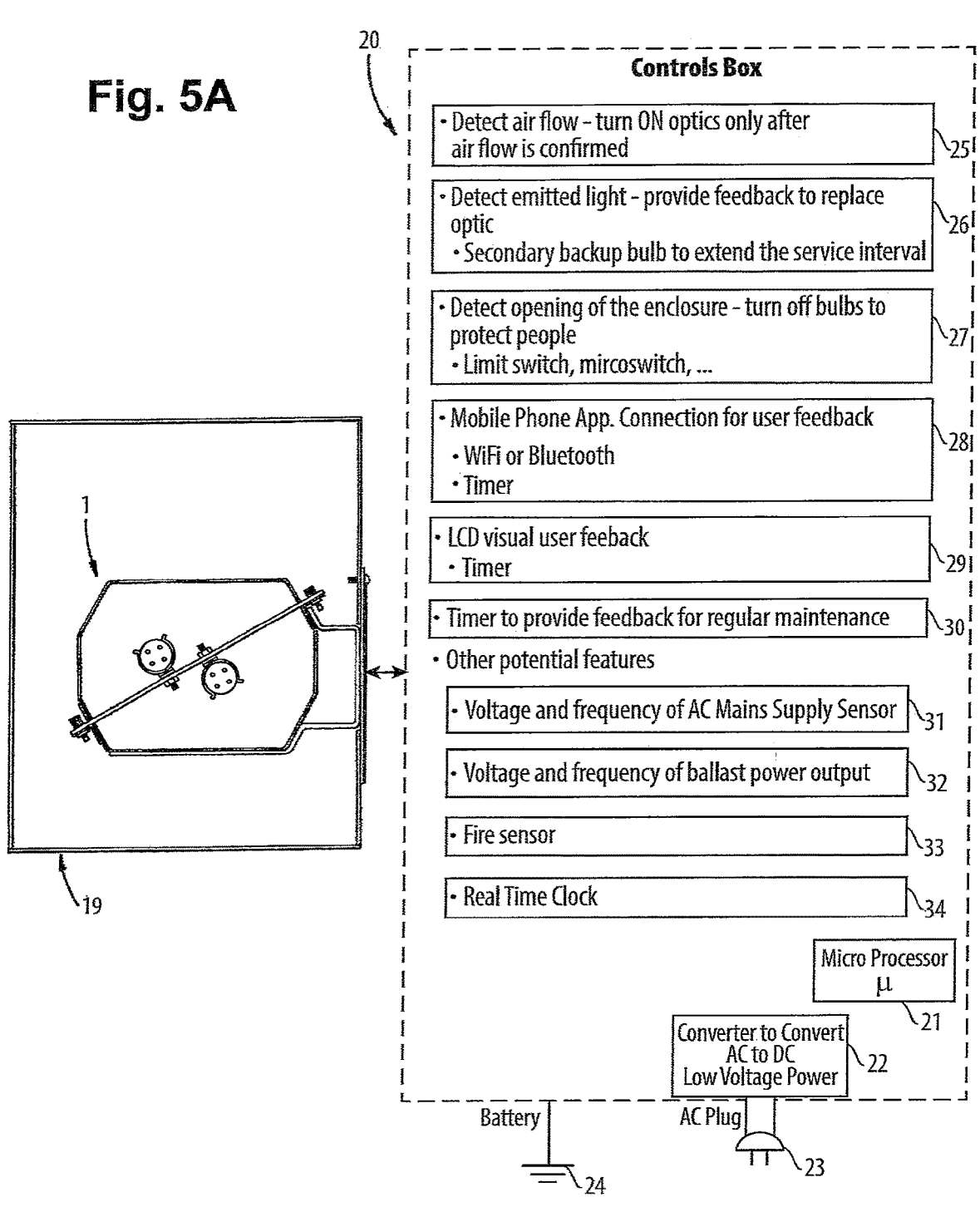
FIG. 5A is a flow chart showing the electronic controls with respect to their position adjacent to the hydroxyl generator.

FIG. 5A is a diagrammatic flow chart, showing the electronic control box 20 of FIGS. 1, 2 and 3, which is also equivalent to the electronic control box 120 of FIG. 4. Adjacent to the hydroxyl generator 1 or 101, which in FIGS. 1-3, the hydroxyl generators are attached by brackets 19 to the electronic control box 20. Similarly, the electronic control box 120 is attached by brackets 119 of FIG. 4.

In the diagrammatic flow chart of FIG. 5A, related to the electrical block diagram of FIG. 5, the control box 20 includes a microprocessor 21 for controlling the sensors and switches, which control the operation of the optics 12 and 13, or 112 and 113, of the hydroxyl generators 1 shown in FIGS. 1-3 and 4 respectively. There is also a power source being either a DC low-voltage battery 24, or an AC plug 23, to provide higher-voltage AC power. When the AC is used, a converter 22 can be provided to convert high-voltage AC to low-voltage DC power for operating any of the sensors and control elements within box 20. Box 25 of FIG. 5A discloses the detector 25 to detect whether airflow is on, so that the optics 12 and 13 will only be on after airflow is confirmed, so that they are not on when there is no airflow. Box 26 of the diagrammatic flow chart of FIG. 5A discloses the sensor 26 for detecting emitted light, and providing feedback to replace optics, including a secondary backup optic, which is also disclosed in box 26 of the flowchart of FIG. 5A. Box 27 of the diagrammatic flow chart of FIG. 5A discloses a detector with a proximity switch 27 detecting opening of the enclosure, and thereafter used to turn off the optics 12 and 13, to protect people from being exposed to the possible harmful UV light emitted from the optics 12 and 13. This detector with the proximity switch 27 shown in box 27 of the diagrammatic flow chart of FIG. 5A also includes a limit switch, a micro switch and sensors. Box 28 of the diagrammatic flow chart of FIG. 5A discloses the mobile phone application connection 28 for user feedback by wireless communication, such as Wi-Fi or Bluetooth® communications, between the operator, the control box 20 and hydroxyl generator 1 itself, together with a timer. The control box 20 also includes the LCD user feedback system 29, with a timer shown in box 29 of the diagrammatic flow chart of FIG. 5A with a timer, as well as a further timer 30 shown in box 30 of the diagrammatic flow chart of FIG. 5A, to provide feedback for regular maintenance. The voltage and frequency of AC main supply sensor 31 is shown in box 31 of the diagrammatic flow chart of FIG. 5A, Box 32 of the diagrammatic flow chart of FIG. 5A shows the voltage and frequency of the monitor of the ballast power outfit 32. Box 33 of the diagrammatic flow chart of FIG. 5A discloses a fire sensor 33, which detects excess heat in the system. Box 34 of the diagrammatic flow chart of FIG. 5A discloses a real time clock 34 which controls any fans providing and activating the airflow through the polygon hydroxyl generators 1.

Figure 5B:
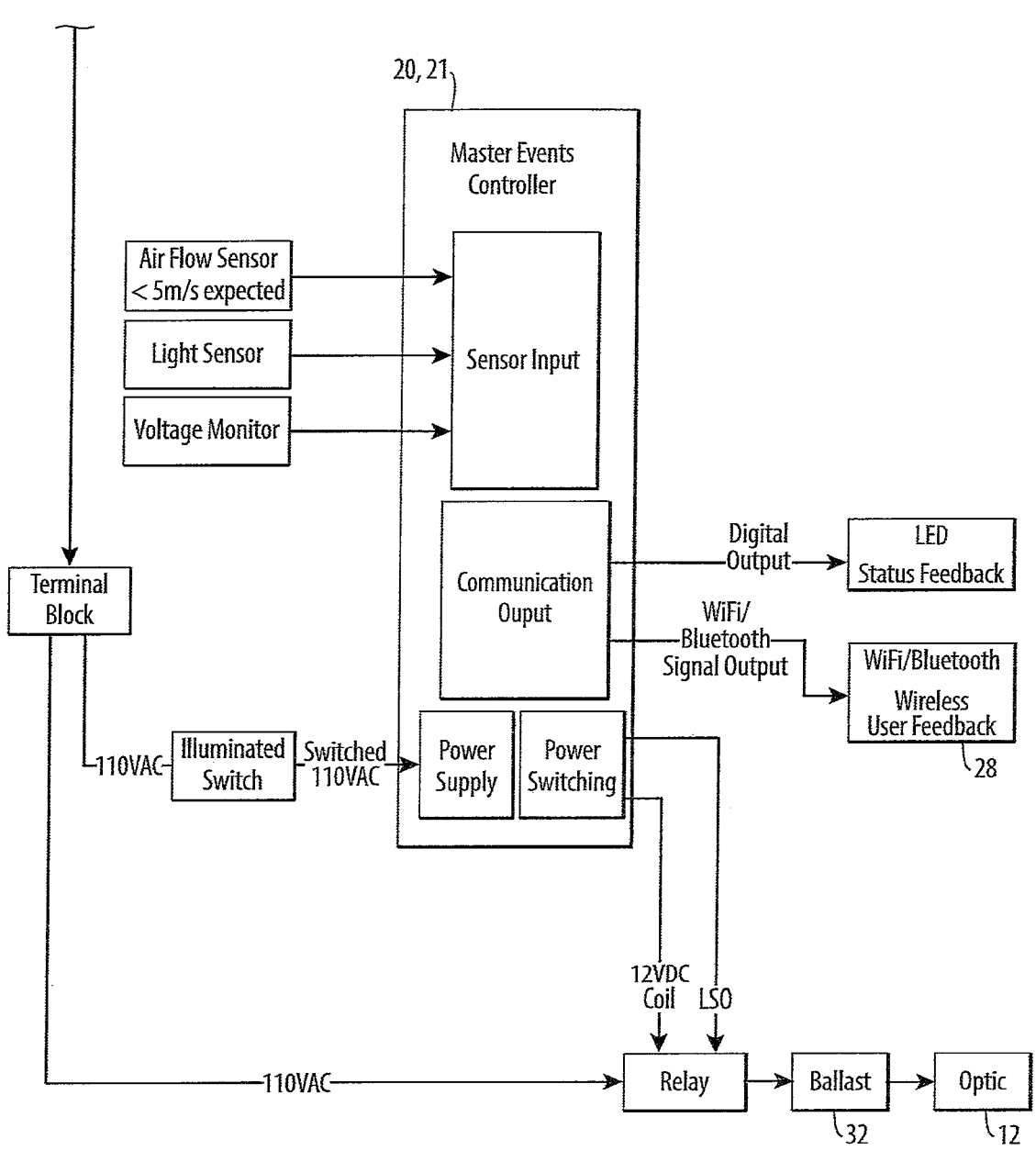
FIG. 5B is a block diagram of the electronic controls of the hydroxyl generator

In the alternate embodiment shown in block diagram FIG. 5B, there are disclosed therein shown the following differences of block diagram FIG. 5B from block diagram FIG. 5, wherein in block diagram FIG. 5B the following features are shown:

1. The key switch (22a) can alternatively be positioned before the power supply (22);
    2. The key switch (22a) can alternatively be a push-button;
3. The power supply (22) can alternatively be included in the Master Events Controller (MEC) 20;
4. The user feedback display (29) of FIG. 5 is not needed in FIG. 5B, because the Wi-Fi/Bluetooth communication works with a mobile application;
5. The PWM Speed controlled fan (34) of FIG. 5 is not needed, because the hydroxyl generator 1 will be located in an existing duct with moving air; and, 6. The power to the relay (not numbered) in FIG. 5 can alternatively be provided by the Master Events Controller (MEC) 20 in FIG. 5B.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

We claim:

1. A combination hydroxyl generator and control system comprising:

a master events controller configured to control operation of said hydroxyl generator;

a housing, said housing being elongated and configured to extend in an axial direction from a first end to a second end to form a length of said housing, and said housing comprising: an air inlet opening at said first end, and an air outlet opening at said second end, and being configured to accommodate a flow of air;

wherein said elongated housing is formed with an octagonal cross-sectional shape;

at least one UV lamp, each configured to extend from a first end to a second end to form a length of each said UV lamp;

wherein said at least one UV lamp is configured to emit ultraviolet light in the spectrum from 100 nanometers to 400 nanometers, to generate hydroxyl radicals from water vapor contained within the flow of air, the hydroxyl radicals being usable to deactivate volatile organic chemicals (VOCs), viruses, bacteria, mold, and pathogens;

wherein said length of said at least one UV lamp is configured to extend an entirety of said length of said housing;

wherein the interior surface of each side of said elongated housing formed by said octagonal cross-sectional shape is configured to reflect the hydroxyl radicals to create a confined space that in combination with said at least one UV lamp in configured to form a reaction chamber, to enhance purification of the air in the flow of air passing therethrough using the hydroxyl radicals;

a first lamp bracket configured to mount in proximity to said first end of said housing;

a second lamp bracket configured to mount in proximity to said second end of said housing;

at least one spring clasp secured to said first lamp bracket;

at least one spring clasp secured to said second lamp bracket; and wherein said at least one spring clasp secured to said first lamp bracket and said at least one spring clasp secured to said second lamp bracket are configured to respectively mount said at least one UV lamp to extend substantially from said first end of said housing, being positioned at said air inlet opening, to said second end of said housing, being positioned at said air outlet opening, with an axial direction of each UV lamp being parallel to the axial direction of said housing, and with each end of said at least one UV lamp being positioned within the flow of air within said octagonal cross-sectional shape of said elongated housing.

2. The combination of claim 1, further comprising:

one or more sensors;

wherein master events controller is configured to receive input from said one or more sensors;

wherein said one or more sensors comprises: an air flow sensor for detecting air flow through said hydroxyl generator, a light sensor for detecting UV light, and a voltage monitor sensor; and said master events controller also having:

(a) a power supply for sending data via a relay for providing power to said at least one UV lamp within said hydroxyl generator; and (b) a communication output comprising a WiFi/bluetooth signal output with wireless user feedback and a digital output with an LED status feedback; and whereby exposure of ambient water vapor in breathable air to optics irradiating UV light within said hydroxyl generator causes atmospheric hydroxyl radicals to form, said hydroxyl radicals deactivating/neutralizing impurities including VOC, virus, bacteria and fungi in breathable air.

3. The combination of claim 2 in which said master events controller is inside of a control box mounted on an outer surface of a wall, said housing for said hydroxyl generator being mounted on an inner surface of said wall adjacent said control box.

4. The combination of claim 3 further comprising:

one or more switches;

wherein said control box includes a microprocessor for controlling said one or more sensors and said one or more switches to control operation of said at least one UV lamp, including the turning off of said at least one UV lamp when said housing is opened to protect people from being exposed to UV light.

5. The combination of claim 4 in which said control box also contains a power source for said hydroxyl generator.

6. The combination of claim 5 in which said control box also includes a timer to provide feedback for regular maintenance.

7. The combination of claim 1 having a fire sensor for detecting excess heat.

8. The combination of claim 1 having a fan control for providing and activating airflow through said hydroxyl generator.

9. The combination of claim 5 in which said power source is either a DC low voltage battery or an AC power plug.

10. The combination of claim 9 having an on/off key power switch.

11. The combination of claim 10 in which said key power switch is a pushbutton switch.

*   *   *   *   *